| United States Patent [19] | [11] Patent Number: 4,831,200 |
| Debras et al. | [45] Date of Patent: May 16, 1989 |

[54] PROCESS FOR THE SELECTIVE HYDROGENATION OF ALKYNES

[75] Inventors: Guy L. G. Debras, Les Bons Villers; Georges E. M. J. De Clippeleir, Sint-Pieters-Leeuw; Jacques F. Grootjans, Leefdael; Raymond M. Cahen, Bruxelles, all of Belgium

[73] Assignee: Labofina, S.A., Brussels, Belgium

[21] Appl. No.: 139,507

[22] Filed: Dec. 30, 1987

[30] Foreign Application Priority Data

Dec. 30, 1986 [GB] United Kingdom ............... 8631018

[51] Int. Cl.$^4$ .............................................. C07C 5/03
[52] U.S. Cl. ............................................... 585/259
[58] Field of Search ..................................... 585/259

[56] References Cited

U.S. PATENT DOCUMENTS

| 3,859,377 | 1/1975 | Gross et al. | 585/260 |
| 3,898,298 | 8/1975 | Desiderio et al. | 585/259 |
| 4,247,725 | 1/1981 | Ohmori et al. | 585/259 |
| 4,367,353 | 1/1983 | Inglis | 585/259 |
| 4,517,395 | 5/1985 | Obenaus et al. | 585/259 |

FOREIGN PATENT DOCUMENTS

| 087980 | 9/1983 | European Pat. Off. . |
| 1063378 | 3/1967 | United Kingdom . |
| 1122018 | 7/1968 | United Kingdom . |
| 1126848 | 9/1968 | United Kingdom . |
| 1424288 | 2/1976 | United Kingdom . |
| 2018817 | 10/1979 | United Kingdom . |
| 2053959 | 2/1981 | United Kingdom . |

*Primary Examiner*—Curtis R. Davis
*Attorney, Agent, or Firm*—Mark A. Montgomery; John K. Abokhair; M. Norwood Cheairs

[57] ABSTRACT

Alkynes are selectively hydrogenated in alkene rich hydrocarbon feeds, such as 1,3-butadiene-rich $C_4$ cuts, by passing the hydrocarbon feed at least partially in liquid phase over a palladium-based catalyst in the presence of hydrogen, preferably in trickle mode, followed by passing the effluent, at least partially in liquid phase preferably containing about 300–400 ppmw alkynes, over a copper-based catalyst in the presence of hydrogen thereby producing a hydrocarbon product of significantly reduced alkyne concentration.

26 Claims, No Drawings

PROCESS FOR THE SELECTIVE HYDROGENATION OF ALKYNES

BACKGROUND OF THE INVENTION

The present invention relates to an improved process for removing alkynes from alkene rich liquid hydrocarbon streams, such as 1,3-butadiene-rich $C_4$ cuts, with a minimum loss of conjugated dienes present therein. In a particular aspect, the present invention relates to a process for the selective hydrogenation of alkynes present in 1,3-butadiene-rich $C_4$ cuts obtained from steam cracking units, to produce a 1,3-butadiene rich product for use in the production of synthetic rubber.

The polymerization of 1,3-butadiene to produce synthetic rubber is an important indusrial process, with over 10 million tons being produced annually. The typical feed stocks used in the production of polybutadiene synthetic rubber contain a major proportion of 1,3-butadiene and butenes. In addition to 1,3-butadiene and butenes, these feedstocks contain significant amounts of alkynes (also called acetylenes) that must be removed prior to polymerization since alkynes poison the polymerization catalyst. The alkynes are generally removed from these feedstocks by selective hydrogenation while trying to avoid or to limit losses in 1,3-butadiene.

The process for the selective hydrogenation of alkynes must be very selective towards alkynes since highly undesirable side reactions occur. These undesirable side reactions include the polymerization and hydrogenation of olefins present in the feed such as 1,3-butadiene and butenes. Not only do these side reactions reduce the amount of desired 1,3-butadiene present in the product but they also reduce catalyst life, due to the buildup of polymer on the catalyst. Regenerations of the catalyst are possible, but are costly and induce catalyst modification that eventually leads to mechanical breakdown of the catalyst pellets which results in higher pressure drops across the bed.

It has long been known to selectively hydrogenate alkynes at high temperature in vapor phase over a copper-nickel catalyst on a $SiO_2/Al_2O_3$ support. However, such processes have fallen to disfavor since the catalyst has to be replaced or regenerated frequently, and the loss of 1,3-butadiene and retention of alkynes is unacceptably high.

U.S. Pat. No. 4,493,906 discloses a catalyst for the removal of alkynes from liquid hydrocarbon streams. The catalyst disclosed in this patent is made of finely divided copper metal dispersed upon a well-defined gamma alumina (which may contain up to 35 wt. % alpha alumina). This gamma alumina has a surface area of 68 to 350 $m^2/g$ with 40 to 98% of the pores having a pore diameter between 4 and 12 nanometers (nm), and 2 to 25% of the pores having a pore diameter between 100 and 1,000 nm. The support is high purity alumina, having less than 0.13 wt. % silicon and less than 0.15 wt. % sodium. This patent discloses that 0 ppm alkynes remain when a feed is treated at about 68° C. with a liquid hourly space velocity (LHSV) lower than 1. However, the corresponding cycle life of the catalyst is only 5½ days; after 6 days, about 100 ppm alkynes are detected in the effluent. It is evident that at higher values of LHSV the cycle life of the catalyst would be even shorter and/or the alkynes removal would be incomplete.

Another type of catalyst known for the selective hydrogenation of alkynes uses a Group VIII B metal in the catalyst. Palladium is the Group VIII B metal that is generally used since it is most active and selective for the hydrogenation of alkynes. However, at least 2 types of operating problems are encountered using this catalyst;

significant loss of 1,3-butadiene even at moderate conversion of alkynes; and reduced catalyst life, due to significant loss of palladium, as clearly disclosed in Hydrocarbon Processing, March 1985, p. 52.

A new palladium catalyst is disclosed in GB No. 2,018,817. This new catalyst is not as rapidly deactivated and does not lose as much palladium as conventional catalysts, and is sometimes used with a conventional catalyst in two successive beds. However, the process using this new catalyst, even in combination with other known catalysts, does not sufficiently reduce the alkyne concentration of the effluent.

In the past few years the severity of steam cracking conditions has increased, resulting in raw $C_4$ cuts that contain an increased concentration of alkynes, up to 1 wt. % or even higher. In addition, the demand for hydrocarbon effluents that contain even less alkynes has increased. Accordingly there is a need in the art for an improved process of removing alkynes from liquid hydrocarbon streams without significantly reducing the alkenes present therein.

OBJECTS OF THE INVENTION

It is an object of the present invention to provide an improved process for removing alkynes from hydrocarbon streams.

It is a more specific object of the present invention to provide a process for removing alkynes from hydrocarbon streams down to less than 30 ppm.

It is another object of the present invention to provide a process for the removal of alkynes from hydrocarbon streams, wherein the catalyst life is greatly increased.

It is still another object of the present invention to provide a process for removing alkynes from hydrocarbon streams with a minimal loss of the other components present therein.

It is yet a further object of the present invention to provide a process for the selective hydrogenation of essentially all alkynes present in 1,3-butadiene rich $C_4$ cuts obtained from steam cracking units.

SUMMARY OF THE INVENTION

In accordance with the present invention, applicants have discovered an improved process for the selective hydrogenation of alkynes present in 1,3-butadiene-rich $C_4$ cuts resulting from steam cracking units.

The process according to the present invention for selective hydrogenation of alkynes present in an alkene rich feed, such as a 1,3-butadiene-rich $C_4$ cut, entails sequentially passing the feed in the presence of hydrogen over a palladium-based catalyst, then a copper-based catalyst, and recovering an alkene rich product of reduced alkyne content.

In a preferred specific aspect of this invention, alkynes present in a 1,3-butadiene-rich $C_4$ cut are selectively hydrogenated in the presence of hydrogen by sequentially passing the 1,3-butadiene-rich $C_4$ cut, maintained in trickle mode, over a palladium-based catalyst, then a copper-based catalyst, and recovering a 1,3- butadiene-rich product of reduced alkyne concentration.

DETAILED DESCRIPTION OF THE INVENTION

The process according to the present invention for the selective hydrogenation of alkynes present in 1,3-butadiene-rich $C_4$ cuts comprises the steps of:

(a) providing a 1,3-butadiene-rich $C_4$ cut;

(b) passing said cut over a palladium-based catalyst in the presence of hydrogen;

(c) passing the liquid effluent from step (b) over a copper-based catalyst in the presence of hydrogen; and (d) recovering a 1,3-butadiene-rich product of reduced alkyne concentration.

A preferred process according to the present invention for the selective hydrogenation of alkynes present in a 1,3-butadiene-rich $C_4$ cut comprises the steps of:

(a) providing a 1,3-butadiene-rich $C_4$ cut;

(b) passing said cut maintained in trickle mode over a palladium-based catalyst bed in the presence of hydrogen;

(c) passing the effluent from step (b) at least partially in the liquid phase over a copper-based catalyst bed in the presence of hydrogen;

(d) separating the residual hydrogen from the remainder of the effluent of step (c); and (e) recovering a 1,3-butadiene-rich product of reduced alkyne concentration.

The applicants have unexpectedly discovered that the selective hydrogenation of alkynes is much more selective when a hydrocarbon feed is sequentially passed over a palladium-based catalyst and a copper-based catalyst. Increase selectivity as used herein means that for a given feed, less 1,3-butadiene is lost for a given level of alkynes hydrogenated.

The palladium-based catalysts used in the process of the present invention are well known in the art. These catalyst have active palladium metal deposited on high purity alumina supports. These catalysts are calcined at temperatures below 600° C., for example from 200°–500° C., preferably 300°–450° C., in neutral, reducing or oxidizing atmosphere and have palladium crystallites with an average size of 45 or at most 50 angstroms.

The catalyst of the present invention preferably contains about 0.1 to 0.35 wt. % active palladium metal, more preferably about 0.2 wt. %. The alumina is of high purity, with the concentration of heavy metals, other than palladium, being less than about 0.05 wt. %.

The surface area of the catalyst is preferably about 50 to 110 $m^2/g$ more preferably about 65 to 95 $m^2/g$. The volume of the catalyst pores is preferably about 0.5 to 0.6 $cm^3/g$ and the catalyst is preferably in the form of spheres about 2 to 4 mm in size.

In conventional selective hydrogenation processes the acidity of the alumina influences the undesired oligomerization reactions and therefore gamma-alumina was generally preferred over conventional eta-alumina. However, this is not required by the process of the present invention, since the acidity of the alumina effects only the long-term stability, and not the activity of a fresh or regenerated catalyst. Other types of alumina may also be used, such as Q-type alumina, as disclosed in Japanese patent application JP-58,017,835.

The use of stabilized or promoted palladium-based catalysts in the process of the present invention is optional and will, therefore, depend upon the activity and long term stability requirements. These catalysts such as palladium-gold supported catalyst are disclosed in European Pat. No. EP-89,252. The activity of these catalysts is usually lower than that of palladium-based catalysts, possibly due to the less homogeneous dispersion of the metals on the support since it is difficult to obtain a controlled bimetallic catalyst at the lower loading levels used for industrial precious metal catalysts. Additionally, the carrier must be suitable for appropriate interaction between the metals, and a well dispersed bimetallic species must be obtained and then maintained during the reaction.

The activation, start-up and regeneration procedures of the palladium-based catalyst are known in the art. The activation conists of (i) purging the oxygen with the use of nitrogen, and (ii) passing hydrogen at atmospheric pressure while gradually heating up to about 90° C. then cooling. The start-up procedure consists of slowly increasing the hydrogen pressure, followed by increasing the feed and hydrogen flow rates, and finally increasing the temperature. The regeneration procedure consists of passing steam under atmospheric pressure while gradually increasing the temperature to about 400° C., then holding this temperature and atmospheric pressure while continuing to pass steam for about 2 hours, and finally gradually adding up to several mole percent air to said steam. During the regeneration procedure, the catalyst temperature should not exceed about 500° C. since higher temperatures will adversely affect the palladium in the catalyst. The regeneration is complete when the $CO_2$ content at the exit is sufficiently low.

Prior to the present invention, the typical process conditions recommended in the art for the selective hydrogenation of vinyl and ethylacetylene in a liquid 1,3-butadiene-rich $C_4$ cut, using palladium-catalysts were as follows:

temperature: 15° to 20° C. (inlet)
pressure: 0.5 MPa (5 bar, 0.1 MegaPascal=1 bar)
LHSV: 30 $1/1.h^{-1}$
$H_2$/alkynes molar ratio: 2:1

The typical results obtained with these conditions are:

feed:
    1,3-butadiene 50 vol. %
    ethyl acetylene 0.2 vol. %
    vinyl acetylene 1.2 vol. %
    balance=butenes
purified effluent:
    500 ppm total alkynes 3% butadiene loss
cycle life: 8 to 10 months The copper-based catalysts used in the process of the present invention are also well known in the art. These catalysts usually contain 3 to 13 wt. % finely divided copper dispersed on high-purity aluminum oxide support. U.S. Pat. No. 4,493,906, cited above, discloses the copper-based catalyst and improved catalysts.

Prior to the present invention, the typical process conditions recommended for the selective hydrogenation of vinyl and ethylacetylene in a liquid 1,3-butadiene-rich $C_4$ cut, using copper-based catalysts were as follows:

activation by overnight hydrogenation at 300° to 350° C.,
temperature: 68° C. (inlet)
pressure 2 to 2.5 MPa (20 to 25 bars)
LHSV: 0.67
$H_2$/alkynes molar ratio: 3:1

The typical results obtained with these conditions are:
61 wt. 1,3-butadiene
8716 ppm alkynes
purified effluent:
    60.5 wt. % 1,3-butadiene 0 ppm alkynes
cycle length: 5½ days The use of stabilized or promoted copper-based catalyst are known in the art, examples of which are disclosed in European patent application No. EP-139051. The activity of these catalyst are quite comparable with those of the "unpromoted" copper-based catalyst, and both can be used in the process of the present invention.

The applicants have unexpectedly found that the selective hydrogenation process could be improved by combining two successive reactors, the first of which contains a palladium-based catalyst and the second contains a copper-based catalyst. It has been found hhat through the use of this combination the selectivity is very high and is maintained during very long run times. Accordingly, the improved process of the present invention produces an effluent with very low residual alkynes concentration while keeping the 1,3-butadiene losses to a minimun. In addition, the improved process of the present invention requires both lesser amounts of catalysts and less frequent regenerations.

The optimal conditions for the hydrogenation over a copper-based catalyst have been found to be as follows. With a 100% $H_2$ flow, the total pressure should preferably be from about 0.4 to 0.9 MPa, more preferably 0.6 to 0.8 MPa. Thus, if refinery hydrogen is used in the process of the present invention, the total pressure should be slightly higher since refinery hydrogen usually contains about 75% hydrogen and about 25% methane. The inlet temperature of the feed should be sufficiently low to keep the feed at least partially in the liquid phase, preferably about 45° to 70° C.

The liquid hourly space velocity (LHSV) should be less than about 6 l per 1 of copper-based catalyst per hour, preferably about 5.5 l/l.h. In this step, the hydrogen/alkynes molar ratio should be at least 5:1, but there is no upper limit for this ratio since the 1,3-butadiene loss does not exceed 0.5 wt. % of its initial concentration. However, under these conditions when the feed to the copper-based catalyst contains more than 300–400 ppmw of alkynes, the residual concentration of alkynes in the final effluent is high.

At the laboratory scale, it is possible to reduce the LHSV so that the feed could contain more than 300–400 ppmw of alkynes. However, when the feed contains up to 1 wt. % or higher alkynes, the LHSV that would be required would be so low as to render industrial applications impractical, since the purification of a sufficient amount of 1,3-butadiene-rich feed for a rubber plant would require extremely large vessels. Also, the required pressure would have to be considerably increased, making industrial applications even more impractical.

Applicants have unexpectedly found that an improved selective hydrogenation process entails reducing the initial alkynes concentration to about 300–400 ppmw by selectively hydrogenating the feed over a palladium-based catalyst prior to passing the feed over the copper-based catalyst. The operation conditions for this initial step are preferably the following:

total pressure: about 0.4 to 0.9 MPa, preferably about 0.6 to 0.8 MPa;
hydrogen/alkynes molar ratio: about 2:1 to 20:1, preferably about 4:1 to 10:1, most preferably about 6:1;
inlet temperature: adjusted with respect to the total pressure in order to maintain the feed at least partially in the liquid phase.

Using these preferred conditions, the LHSV of the feed should be adjusted in such way that the alkynes concentration after passing over the palladium-based catalyst is below about 500 ppmw more preferably between about 300–400 ppmw. This is usually obtained by using an LHSV value of about 15.

In the process of the present invention, each reactor may be either an isothermal reactor or an adiabatic reactor. The hydrogen may be injected with the feed, although it has been found highly desirable to inject the hydrogen partially with the feed and partially in the course of the process, e.g. at one or several places about half way along the first catalyst bed and at the second reactor inlet. According to an embodiment of the invention, up to 30%, preferably about 15%, of the total hydrogen flow is injected at one or several places, up to the second reactor inlet.

Applicants have unexpectedly found that the palladium-based catalysts are more selective when used in trickle mode than in homogeneous liquid or gas phase. Increased selectivity, as used herein, means that, for a given feed, less 1,3-butadiene is lost for a given level of alkynes hydrogenation. The trickle mode, as used herein, is defined as the operation under such conditions of temperature and pressure that cause the feed to pass as a mixed gaseous-liquid phase over the catalyst. It is preferred that about 10 to 80 wt. % of the feed be in liquid form during this step of the present invention, more preferably about 25 to 70 wt. %.

Since the hydrogenation reaction is exothermal, it is usually more convenient to provide the feed in a liquid state, under conditions very near the gas-liquid equilibrium so that the reaction continues in trickle mode.

If an adiabatic reactor is used as the first reactor, in trickle mode, the heat released by the hydrogenation reaction is compensated by the vaporization of part of the liquid phase. It is thus highly desirable in the case of an adiabatic reactor used in trickle mode to have enough feedstock in the liquid phase at the inlet in order to absorb the heat released, and further to inject part of the feed in the liquid form along the axis of the reactor. According to an embodiment of the invention, up to about 20% of the feed (preferably 5–10%) is injected in liquid form, at one or several places about half way along the catalyst bed in an adiabatic reactor used in trickle mode. Although not wishing to be bound by theory, the applicants believe that these injections possibly serve to maintain the trickle mode conditions constant throughout the adiabatic reactor.

Since the gaseous phase is produced partially by the vaporization of the feed, the trickle mode is usually operated in co-current mode. Although it is possible to operate in up-flow mode, the applicants have found that it is highly preferable to operate in downflow mode.

When operating in trickle mode, the reaction temperature (or inlet temperature if an adiabatic reactor is used) is adjusted with respect to the total pressure, in order to maintain the desired trickle mode operation. Within the preferred ranges, lower pressures and/or higher temperatures tend to impart a higher activity to the catalyst.

The LHSV to be used in the process of the present invention is easily determined by one skilled in the art.

As desired, the LHSV is adjusted, within the limits of the specification, to maximize the hydrogenation of alkynes while minimizing olefin loss.

The C$_4$ feeds that can be used in the process of the present invention usually comprise a mixture of normally gaseous hydrocarbons:

| | |
|---|---|
| 1,3-butadiene | 30 to 55%, typically 40 to 50% |
| 1,2-butadiene | up to 2%, typically about 0.2% |
| alkynes (mainly ethyl and vinyl acetylene) | up to 5%, typically up to 1.5% |
| C$_3$ hydrocarbons and heavies | traces |
| butanes | up to 10%, typically up to 5% |
| butenes | balance |

The feeds contemplated to be used in the present invention are those usually obtained from the steam cracking unit. However, other feeds or feeds obtained from other sources may also be used without departing from the scope of the invention, as for example propylene-rich feeds containing methylacetylene as impurity.

The following examples are given in order to illustrate the invention, but are not intended to limit the reasonable scope thereof.

EXAMPLE 1

(a) Preparation of the palladium-based catalyst

The alumina support selected was in the form of spheres having a diameter of 2 to 4 mm and a bulk density of 0.72 g/cm$^3$.

The support was contacted with a solution of palladium acetylacetonate in benzene. The weight ratio of support to solution was 10:16. The concentration by weight of Pd in the solution was 1350 ppmw before contacting the support, and 100 ppmw after 8 hours of impregnation.

The impregnated support was filtered and then dried at 120° C. for 6 hours under an air flow. The support was then heated to 300° C. in a tubular oven, and held first for 2 hours while maintaining the air flow, then, after a nitrogen purge, for a further 2 hours under a hydrogen flow.

After cooling, the catalyst contained 0.2 wt. % of palladium.

(b) Catalyst activation and start-up of the palladium-based catalyst

The catalyst was purged for 1 hour with nitrogen at a gaseous hourly space velocity (GHSV) of 333 l/l.h. Hydrogen under atmospheric pressure was then passed over the catalyst at a GHSV of 200 l/l.h; the catalyst was then heated to 66° C. and held for 0.5 hours, then at 93° C. for 2 hours, and finally cooled to 20° C. The hydrogen used was refinery hydrogen, consisting of a mixture of about 75% hydrogen and about 25% methane.

The hydrogen flow was then increased to 333 l/l.h at a temperature of 26° C. for 35 minutes. The hydrogen pressure was then slowly increased from atmospheric to 0.61 MPa (6.2 kg/cm$^2$) and maintained for 45 minutes. The feed and hydrogen flow rates were then increased to one fourth of nominal, maintained for 50 minutes, increased to half of the nominal values, maintained for 15 minutes, and finally increased to nominal values while raising the temperature to 57° C. at a heating rate of 10° C./h.

(c) Preparation of the copper-based catalyst

A special grade of gamma-alumina was prepared by decomposing triethyl aluminum to alpha aluminum monohydrate, then calcining the alpha aluminum monohydrate to gamma alumina.

The resulting powder was extruded into pellets of about 1.5 mm in diameter and about 6 mm in length. The following properties were determined:

| | |
|---|---|
| % Na$_2$O | 0.015 |
| % Fe$_2$O$_3$ | 0.006 |
| Surface area (m$^2$/g) | 240 |
| Pore volume (cm$^3$/g) | 0.56 |
| Bulk density (g/cm$^3$) | 0.69 |
| Pores < 7.5 nm | 75% |
| Pores < 10 nm | 82% |

The extrudates were impregnated with a solution of 77.8 wt. % 2 Cu(NO$_3$)$_2$.5 H$_2$O in water in a weight ratio extrudates to solution of 20:9. When all the solution had been sorbed, the support was dried overnight at about 110° C., then calcined at 400° C. for about 6 hours.

(d) Activation and start-up of the copper catalyst

The catalyst was purged for 4 hours under atmospheric pressure and at a temperature of 150° C. with nitrogen at a gaseous hourly space velocity (GHSV) of 50 l/l.h. A flow of hydrogen was then added to the nitrogen flow at a GHSV of 5 l/l.h for 24 hours, all other conditions being identical. The temperature was then increased to 280° C. and held for a further 24 hours with continued nitrogen and hydrogen flow, the hydrogen flow was then interrupted and the catalyst was allowed to cool under nitrogen flow.

(e) Alkynes selective hydrogenation

The feed contained:
45.90 wt. % 1,3-butadiene
4890 ppmw vinylacetylene (VAC)
1110 ppmw ethylacetylene (EAC)
1010 ppmw methylacetylene (MAC)
about 50% butenes, about 4% butanes, and traces of other hydrocarbons.

The hydrogenation was carried out in two serial reactors. The first reactor was an adiabatic reactor, containing the palladium-based catalyst, operated in downflow mode. Refinery hydrogen containing about 74% hydrogen was used. The guage pressure was 0.82 MPa (8.2 bar); the inlet temperature was adjusted to 64° C., so that this step was carried out in trickle mode. The feed was injected with a total liquid hourly space velocity (LHSV) corresponding to 24.7 liters of liquid feed per liter of catalyst per hour. However, 8.1% of the feed was injected at a side inlet about half way along the catalyst bed. Hydrogen was injected with the feed, in a hydrogen to feed molar ratio of 0.054 at the main inlet and 0.048 at the side inlet. After the first reactor, a sample was taken. The 1,3-butadiene loss was of 3.1 wt. % of the initial amount, and the sample contained 27 ppmw of VAC and 362 ppmw of EAC.

The second reactor was an adiabatic reactor containing the copper-based catalyst, operated in upflow mode. The inlet temperature was 58° C. and the guage pressure was 0.8 MPa. The feed was passed with a liquid hourly space velocity (LHSV) of 6.0 l/l.h. Hydrogen was injected with the feed, in sufficient amount to reach a hydrogen to akynes molar ratio of 150. The effluent contained less than 5 ppmw (detection limit) of any of VAC, EAC, or MAC. The 1,3-butadiene loss in the second reactor was 0.3 wt. % of the initial amount, and the total 1,3-butadiene loss was thus 3.4 wt. % of said initial amount.

EXAMPLE 2

The experiment described in Example 1 was repeated with a similar feed containing 46.36 wt. % 1,3-butadiene, 7880 ppmw VAC and 1690 ppmw EAC. All experimental conditions were identical, except the following:
(a) first reactor
inlet temperature: 66° C.
feed injected at the main inlet: 100%
LHSV: 14.7 1/l.h
$H_2$: feed molar ratio: 0.047
(b) second reactor
inlet temperature: 56° C.
LHSV: 6.1 1/l.h
$H_2$: alkynes molar ratio: 120

After the first reactor, the 1,3-butadiene loss was 2.6 wt. % of the initial amount, and the effluent contained <5 ppmw VAC and 286 ppmw EAC.

After the second reactor, the 1,3-butadiene loss was 0.3 wt. %, and the effluent contained <5 ppmw VAC and <5 ppmw EAC. The total 1,3-butadiene loss was thus 2.9 wt. % of the initial amount.

COMPARATIVE EXAMPLE A

A palladium-based catalyst was prepared according to the procedure described in Example 1, and its activation and start-up were likewise carried out.

The feed contained:
46.99 wt. % butadiene
7140 ppmw VAC
1680 ppmw EAC
47.89 wt. % butenes
3.74 wt. % butanes
the balancing consisting of other hydrocarbons.

The hydrogenation was carried out in an isothermal reactor, containing the palladium-based catalyst, operated in downflow mode. The pressure was 0.5 MPa (5 bar) and the temperature was 20° C. The LHSV of the feed was 30 1/l.h. Pure hydrogen was injected with the feed, in a hydrogen to feed molar ratio of 0.04.

The 1,3-butadiene loss was 3 wt. % of the initial amount, and the effluent contained more than 500 ppmw of each of VAC and EAC.

This example shows that the conditions usually recommended in the art do not obtain sufficiently low residual alkynes concentrations, down to 100 ppmw and below.

COMPARATIVE EXAMPLE B

The experiment described in comparative Example A was repeated with different hydrogenation conditions.

The hydrogenation was carried out in an adiabatic reactor, operated in downflow mode using pure hydrogen. The inlet temperature was 50.5° C. The feed LHSV was 14.2, and the hydrogen to feed molar ratio was 1:20.

The results are shown in Table 1.

TABLE

| | Feed | Effluent A | Effluent B | Effluent C |
|---|---|---|---|---|
| Pressure | | 0.61 | 0.69 | 0.78 MPa |
| Composition | | | | |
| 1,3-butadiene | 46.99 | 44.23 | 43.98 | 43.71 wt. % |
| VAC | 7140 | 109 | 258 | 487 ppmw |
| EAC | 1680 | 282 | 375 | 455 ppmw |
| butanes | 3.74 | 3.75 | 3.77 | 3.79 wt. % |
| butenes | 47.89 | 51.60 | 51.78 | 52.02 wt. % |
| other hydrocarbons | balance | balance | balance | balance |

This example shows that, despite considerable 1,3-butadiene losses, the effluent still contained significant amounts of VAC and EAC.

COMPARATIVE EXAMPLE C

A palladium-based catalyst was prepared according to the procedure described in Example 1, and its activation and start-up were likewise carried out.

The feed contained:
41.04 wt. % 1,3-butadiene,
7280 ppmw VAC,
1640 ppmw EAC,
45.91 wt. % butenes,
8.71 wt. % butanes,
the balance consisting of other hydrocarbons.

The hydrogenation was carried out in an adiabatic reactor, containing the palladium-based catalyst, operated in downflow mode using refinery hydrogen. The pressure was of 0.8 MPa (8 bars); the temperature was adjusted to 66° C. so that this step was carried out in trickle mode. The feed was injected with a total LHSV corresponding to 7.2 liters of liquid feed per liter of catalyst per hour. However, 10% of the feed was injected at a side inlet about half way along the catalyst bed. hydrogen was injected with the feed, in a hydrogen to feed molar ratio of 0.081 at the main inlet and 0.15 at the side inlet.

The 1,3-butadiene loss was 8.0 wt. % of the initial amount, and the effluent contained less than 5 ppmw (detection limit) either VAC or EAC.

This example shows that, even though the trickle mode is an improvement over the prior art, the selectivity of palladium-based catalysts when used alone is not as high as when combined with the copper-based catalyst according to the present invention. In this example, the total hydrogenation of VAC and EAC is obtained at the expense of greater 1,3-butadiene losses than the process of the invention.

COMPARATIVE EXAMPLE D

A copper-based catalyst was prepared according to the procedure described in Example 1, and its activation and start-up were likewise carried out.

The feed contained 46.18 wt. % 1,3-butadiene, 7679 ppmw VAC and 1825 ppmw EAC, the balance mainly consisting of butenes.

The hydrogenation was carried out in an adiabatic reactor, containing the copper-based catalyst, operated in upflow mode. The inlet temperature was 51° C., and the pressure was 1.7 MPa (17 bars). The LHSV of the feed was 1 1/l.h. Refinery hydrogen was injected with the feed, in a hydrogen to feed molar ratio of 0.024.

The 1,3-butadiene loss was 3.0 wt. % of the initial amount, and the effluent contained less than 5 ppmw (detection limit) either VAC or EAC.

This example shows that, although a good selectivity can be obtained by using a copper-based catalyst, the process of the invention accomplishes the same results at a lower pressure and a higher LHSV.

Indeed, when using either lower pressures or higher space velocities in experiments similar to this comparative Example D, residual alkynes are detected in the effluent.

COMPARATIVE EXAMPLE E

A palladium-based catalyst and a copper-based catalyst were prepared according to the procedures described in Example 1, and their activation and start-up were likewise carried out.

The feed contained 44.34 wt. % 1,3-butadiene, 7579 ppmw VAC, 1865 ppmw EAC, 49.75 wt. % butenes, 3.95 wt. % butanes, with the balance consisting of other hydrocarbons.

The hydrogenation was carried out in two serial reactors using refinery hydrogen. The first reactor was an adiabatic reactor, containing the copper-based catalyst, operated in downflow mode. The pressure was 0.85 MPa (8.5 bars) add the inlet temperature was 52.4° C. The feed was injected with an LHSV of 1.0 l/l.h, together with hydrogen in a hydrogen to feed molar ratio of 0.023. After the first reactor, the effluent contained 940 ppmw VAC and 1790 ppmw EAC, and the 1,3-butadiene concentration was slightly increased to 44.63 wt. %.

The second reactor was an adiabatic reactor, containing the palladium-based catalyst, operated in downflow mode. The pressure was 0.8 MPa (8 bars), and the inlet temperature was adjusted to 65° C. so that this step was carried out in trickle mode. The feed was injected with a total LHSV corresponding to 7.5 liters of liquid feed per liter of catalyst per hour. Hydrogen was injected with the feed, in order to reach a hydrogen to alkynes molar ratio of 5. The effluent contained less than 5 ppmw (detection limit) of both VAC or EAC. The 1,3-butadiene loss in the second reactor was 8.25 wt. % of the initial amount, and the total 1,3-butadiene loss was thus 7.6 wt. % of the initial amount.

This example shows that a combination of copper and palladium-based catalysts, other than what is required by the present invention, does not give the improvement provided by the process of the invention. Indeed, the total hydrogenation of VAC and EAC could only be reached with (i) greater 1,3-butadiene losses *and* (ii) lower space velocities than with the process of the present invention.

What is claimed is:

1. A process for the selective hydrogenation of alkynes present in an alkene rich feed comprising;
   (a) passing said feed at least partially in a liquid phase over a palladium-based catalyst in the presence of hydrogen then;
   (b) passing the effluent from step (a) at least partially in liquid phase over a copper-based catalyst in the presence of hydrogen; and
   (c) recovering an alkene rich product of reduced alkynes.

2. The process according to claim 1 wherein 1,3-butadiene is present in said alkene rich feed.

3. The process according to claim 1 wherein the residual hydrogen is separated from said feed after being passed over said copper-based catalyst.

4. The process according to claim 1 wherein said feed in step (a) is passed in downflow mode over said palladium-based catalyst in a first catalyst bed in an adiabatic reactor.

5. The process according to claim 4 wherein a portion of said feed is injected in liquid form along said first catalyst bed in an amount sufficient to maintain said feed at least partially in a liquid phase.

6. The process according to claim 5 wherein up to 30% of the total hydrogen used in said process is injected from at least one place along said first catalyst bed.

7. The process according to claim 1 wherein said alkene rich product contains less than 30 ppm alkynes.

8. The process according to claim 7 wherein said alkene rich product contains less than 5 ppm alkynes.

9. The process according to claim 1 wherein the total hydrogen:alkynes molar ratio is from about 2:1 to 20:1 and the hydrogen:alkynes molar ratio in step (b) is greater than about 5:1.

10. The process according to claim 1 wherein the pressure during the selective hydrogenation is between about 0.4 to 0.9 MPa when using a 100% hydrogen flow.

11. The process according to claim 1 wherein said palladium-based catalyst contains about 0.1 to 0.35 wt. % active palladium metal deposited on high-purity alumina.

12. The process according to claim 1 wherein said palladium-based catalyst is stabilized by the use of a bimetallic catalyst.

13. The process according to claim 12 wherein said palladium-based catalyst is stabilized with a palladium-gold alloy deposited on high-purity alumina.

14. The process according to claim 1 wherein the feed is passed in trickle mode over said palladium-based catalyst.

15. The process according to claim 14 wherein about 10 to 80% of said feed is in liquid form during the selective hydrogenation of step (a).

16. The process according to claim 1 wherein the LHSV of the feed in step (a) is adjusted in such a way that the alkynes concentration after passing over said palladium-based catalyst is from about 300 to 400 ppmw.

17. The process according to claim 1 wherein the inlet temperature of the feed in step (b) is between about 45° to 70° C.

18. The process according to claim 1 wherein the LHSV of the feed in step (b) is 6 l/lh.

19. The process according to claim 1 wherein the catalyst in step (b) contains from about 3 to 13 wt. % finely divided copper dispersed on high-purity aluminum oxide support.

20. The process according to claim 19 wherein the aluminum oxide support is prepared by decomposing triethyl aluminum to alpha aluminum monohydrate which is then calcined to gamma alumina.

21. A process for the selective hydrogenation of alkynes present in a 1,3-butadiene-rich $C_4$ cut comprising:
   (a) passing said cut maintained in trickle mode over a palladium-based catalyst in the presence of hydrogen thereby reducing the alkynes present in said cut to below about 500 ppmw;
   (b) passing the effluent from step (a) at least partially in the liquid phase over a copper-based catalyst in the presence of hydrogen; and
   (c) recovering a 1,3-butadiene-rich product of reduced alkyne concentration.

22. The process according to claim 21 wherein said 1,3-butadiene-rich product contains less than 30 ppm alkynes.

23. The process according to claim 22 wherein said 1,3-butadiene-rich product contains less than 5 ppm alkynes.

24. The process according to claim 21 wherein said palladium-based catalyst is stabilized by the use of a bimetallic palladium-gold alloy deposited on high purity alumina.

25. The process according to claim 21 wherein said cut is passed over said palladium-based catalyst under temperature and pressure conditions that cause said cut to pass as a mixed gaseous-liquid phase.

26. The process according to claim 25 wherein about 10-18% of said cut is in liquid form during step (a).

* * * * *